United States Patent [19]

Lesher et al.

[11] 4,420,617
[45] Dec. 13, 1983

[54] 5(PYRIDINYL)PYRIDIN-2-AMINES

[75] Inventors: George Y. Lesher; Chester J. Opalka, Jr., both of Schodack; Donald F. Page, East Greenbush, all of N.Y.

[73] Assignee: Sterling Drug Inc., New York, N.Y.

[21] Appl. No.: 395,737

[22] Filed: Jul. 6, 1982

Related U.S. Application Data

[63] Continuation-in-part of Ser. No. 307,778, Oct. 2, 1981, abandoned, which is a continuation-in-part of Ser. No. 135,100, Mar. 28, 1980, Pat. No. 4,297,360.

[51] Int. Cl.$^3$ .......................................... C07D 401/04
[52] U.S. Cl. ............................................... 546/257
[58] Field of Search ........................................ 546/257

[56] References Cited

U.S. PATENT DOCUMENTS 4,297,360 10/1981 Lesher et al. ...................... 546/257
4,331,672 5/1982 Lesher et al. ...................... 546/257

FOREIGN PATENT DOCUMENTS 1322318 7/1973 United Kingdom .

OTHER PUBLICATIONS

D. A. Inoyatova et al., [Chem. Absts. 74, 125,360b (1971); Tr. Samarkand. Gos. Univ. 1969, No. 167, 173–174 (Russ.) from Ref. Zh., Khim 1970, Abstr. No. 5Zh482].

*Primary Examiner*—John M. Ford
*Attorney, Agent, or Firm*—Robert K. Bair; B. Woodrow Wyatt; Paul E. Dupont

[57] ABSTRACT

5-PY-6-Q-pyridin-2-amines (I) or pharmaceutically acceptable acid-addition salts thereof are useful cardiotonics, where Q is hydrogen or lower-alkyl, and PY is 4-pyridinyl or 4-pyridinyl having one or two lower-alkyl substituents. Their preparation from the corresponding 5-PY-6-Q-2(1H-pyridinones via the corresponding 2-halo-5-PY-6-Q-pyridines is shown.

5 Claims, No Drawings

5(PYRIDINYL)PYRIDIN-2-AMINES

CROSS-REFERENCE TO RELATED APPLICATION

This application is a continuation-in-part of copending application Ser. No. 307,778, filed Oct. 2, 1981, now abandoned, in turn, a continuation-in-part of its copending application Ser. No. 135,100, filed Mar. 28, 1980 and now U.S. Pat. No. 4,297,360, issued Oct. 27, 1981.

Lesher, Opalka and Page application Ser. No. 135,211, filed Mar. 28, 1980 and now U.S. Pat. No. 4,276,293, issued June 30, 1981, discloses as an intermediate 5-(4-pyridinyl)pyridin-2-amine.

BACKGROUND OF THE INVENTION (a) Field of the Invention

This invention relates to 5-(pyridinyl)pyridin-2-amines, useful as cardiotonics.

(b) Description of the Prior Art

Lesher and Gruett British Pat. No. 1,322,318, published July 4, 1973, shows as intermediates for preparing antibacterially active 1-alkyl-1,4-dihydro-4-oxo-7-PY-1,8-naphthyridine-3-carboxylic acids and esters (where PY is 4- or 3-pyridinyl or 4- or 3-pyridinyl having one or two lower-alkyl substituents) 2-amino-6-(4- or 3-pyridinyl)pyridine, alternatively named 6-(4- or 3-pyridinyl)pyridin-2-amines.

D. A. Inoyatova et al. [Chem. Absts. 74, 125,360b (1971); Tr. Samarkand. Gos. Univ. 1969, No. 167, 173-4 (Russ.) From Ref. Zh., Khim 1970, Abstr. No. 5Zh482] report the amination of 3,3'-bipyridine and subsequent thin-layer chromatography using diethyl ether to produce 6-amino-3,3'-bipyridine, alternatively named 5-(3-pyridinyl)pyridin-2-amine.

SUMMARY OF THE INVENTION

In a composition of matter aspect, the invention resides in 5-PY-6-Q-pyridin-2-amines (I) or pharmaceutically acceptable acid-addition salts thereof, which are useful as cardiotonic agents, where PY and Q are defined hereinbelow.

DETAILED DESCRIPTION INCLUSIVE OF PREFERRED EMBODIMENTS

In a composition of matter aspect the invention resides in a 5-PY-6-Q-pyridin-2-amine having the formula I

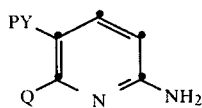

or pharmaceutically acceptable acid-addition salt thereof, where Q is hydrogen or lower-alkyl, and PY is 4-pyridinyl or 4-pyridinyl having one or two lower-alkyl substituents. The compounds of formula I, as shown hereinbelow, are useful as cardiotonic agents. Preferred embodiments of the compounds of formula I are those where Q is hydrogen, methyl or ethyl, and PY is 4-pyridinyl. A particularly preferred embodiment is 6-methyl-5-(4-pyridinyl)pyridin-2-amine or pharmaceutically acceptable acid-addition salt thereof.

The term "lower-alkyl" as used herein, e.g., as one of the meanings for Q or as a substituent for PY in formula I, means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY in formula I where PY is 4-pyridinyl having one or two lower-alkyl substituents are the following: 2-methyl-4-pyridinyl, 2,6-dimethyl-4-pyridinyl, 3-methyl-4-pyridinyl, 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diisopropyl-4-pyridinyl, 2,6-di-n-hexyl-4-pyridinyl, and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form; however, appropriate pharmaceutically acceptable salts within the scope of the invention are those derived from mineral acids such as hydrochloric acid, hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, acetate, citrate, lactate, tartrate, methanesulfonate, ethanesulfonate, benzenesulfonate, cyclohexylsulfamate and quinate respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds of formula I are preferred, all acid-addition salts are within the scope of the invention. All acid-addition salts are useful as sources of the free base form even if the particular salt per se is desired as in intermediate product as for example when the salt is formed only for purposes of purification or identification, or when it is used as an intermediate in preparing a pharmaceutically acceptable salt by ion exchange procedures.

The molecular structure of the compound of formula I was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same.

The reaction of a 5-PY-6-Q-2(1H)-pyridinone (II) with an inorganic halogenating agent to produce a 2- halo-5-PY-6-Q-pyridine (III) is preferably carried out by refluxing the 2(2H)-pyridinone (II) with excess phosphorus oxychloride containing a catalytic amount of dimethylformamide to obtain the 2-chloro compound. Other suitable inorganic halogenating agents include $PCl_3$, $POBr_3$, $PCl_5$, diphenylphosphonic dichloride, and the like.

The reaction of the 2-halo compound (III) with ammonia to produce I is run by heating the reactants, preferably under pressure using ammonia or source thereof. The reaction of III with hydrazine is similarly run to obtain the corresponding 2-hydrazino derivatives, which are readily converted by catalytic hydrogenation to the corresponding 2-amines (I).

The intermediate 5-PY-6-Q-2(1H)-pyridinones (II) where Q is hydrogen and their preparation are shown in Lesher and Opalka U.S. Pat. No. 4,072,746, issued Feb. 7, 1978; and, the intermediate 5-PY-6-Q-2(1H)-pyridinones (II) where Q is lower-alkyl are shown in Lesher, Opalka and Page U.S. Pat. No. 4,276,293, issued June 30, 1981.

The following examples will further illustrate the invention without, however, limiting it thereto.

A. 2-HALO-5-PY-6-Q-PYRIDINES

A-1. 2-Chloro-5-(4-pyridinyl)pyridine, alternatively named 6-chloro-[3,4'-bipyridine]–A mixture containing 105 g. of 5-(4-pyridinyl)-2(1H)-pyridinone and 1 liter of phosphorus oxychloride was heated on a steam bath for two hours and then allowed to stand at room temperature overnight. The excess phosphorus oxychloride was distilled off in vacuo and the remaining material poured into ice. The aqueous mixture was made weakly basic with ammonium hydroxide. The precipitate was collected, washed with water and dried in vacuo at 70° C. to yield 108 g. of 2-chloro-5-(4-pyridinyl)pyridine. A sample of this intermediate recrystallized from methanol using decolorizing charcoal melted at 161°–162° C. with decomposition.

Following the above procedure but using in place of phosphorus oxychloride a molar equivalent quantity of phosphorus oxybromide or phosphorus tribromide, it is contemplated that the corresponding compound of Example A-2 can be obtained.

A-2. 2-Bromo-5-(4-pyridinyl)pyridine.

A-3. 2-Chloro-6-methyl-5-(4-pyridinyl)pyridine, 15.3 g., was obtained following the procedure described in Example A-1 using 18.6 g. of 6-methyl-5-(4-pyridinyl)-2(1H)-pyridinone, 100 ml. of phosphorus oxychloride, 2 ml. of dimethylformamide, a heating period of 24 hours on a steam bath, extraction of the product from the aqueous basified reaction mixture with ethyl acetate and removal of the ethyl acetate by distillation in vacuo. A sample of 2-chloro-6-methyl-5-(4-pyridinyl)pyridine thus obtained was purified by two recrystallizations from small quantities of ethyl acetate using decolorizing charcoal, two recrystallizations from acetonitrile using decolorizing charcoal, the second time drying in vacuo, and found to melt at 105°–106° C.

Following the procedure described in Example A-1 or A-3 but using in place of 5-(4-pyridinyl)-2(1H)-pyridinone or 6-methyl-5-(4-pyridinyl)-2(1H)-pyridinone a molar equivalent quantity of the corresponding 5-PY-6-Q-2(1H)-pyridinone, it is contemplated that the corresponding 2-chloro-5-PY-6-Q-pyridines of Examples A-4 through A-13 can be obtained.

A-4. 2-Chloro-5-(2-methyl-4-pyridinyl)pyridine.
A-5. 2-Chloro-5-(3-ethyl-4-pyridinyl)pyridine.
A-6. 2-Chloro-6-ethyl-5-(4-pyridinyl)pyridine.
A-7. 2-Chloro-6-n-propyl-5-(4-pyridinyl)pyridine.
A-8. 2-Chloro-6-isopropyl-5-(4-pyridinyl)pyridine.
A-9. 6-n-Butyl-2-chloro-5-(4-pyridinyl)pyridine.
A-10. 2-Chloro-6-isobutyl-5-(4-pyridinyl)pyridine.
A-11. 2-Chloro-5-(4-pyridinyl)-6-tert.-butylpyridine.
A-12. 2-Chloro-6-n-pentyl-5-(4-pyridinyl)pyridine.
A-13. 2-Chloro-6-ethyl-5-(2-methyl-4-pyridinyl)pyridine.

B. 5-PY-6-Q-PYRIDIN-2-AMINES

B-1. 5-(4-Pyridinyl)pyridin-2-amine, alternatively names [3,4'-bipyridin]-6-amine—A mixture containing 48 g. of 2-chloro-5-(4-pyridinyl)pyridine and 700 ml. of ammonium hydroxide was heated in an autoclave at 150° C. and 200 p.s.i. for sixteen hours. The solid was collected, washed with water and dried. The filtrate was distilled in vacuo to remove the excess ammonium hydroxide and the remaining residue was combined with the above solid and the combined material was recrystallized from water and dried in vacuo at 70° C. to yield 29 g. of 5-(4-pyridinyl)pyridin-2-amine, m.p. 192°–195° C.

Acid-addition salts of 5-(4-pyridinyl)pyridin-2-amine are conveniently prepared by adding to a mixture of 2 g. of 5-(4-pyridinyl)pyridin-2-amine in about 40 ml. of aqueous methanol the appropriate acid, e.g., methanesulfonic acid, concentrated sulfonic acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 5-(4-pyridinyl)pyridin-2-amine and the appropriate acid, e.g., lactic acid or hydrochloric acid, to prepare respectively the monolactate or monohydrochloride salt in aqueous solution.

B-2. 6-Methyl-5-(4-pyridinyl)pyridin-2-amine—A mixture containing 17.4 g. of 2-chloro-6-methyl-5-(4-pyridinyl)pyridine and 60 ml. of 95% hydrazine was heated on a steam bath for 24 hours and chilled. The separated solid was collected by filtration and washed successively with water and acetonitrile to yield 15.8 g. of [6-methyl-5-(4-pyridinyl)pyridin-2-yl]hydrazine, which was used directly without further purification to prepare the corresponding substituted-pyridin-2-amine as described in the following paragraph. A sample 6-methyl-5-(4-pyridinyl)pyridine-2-hydrazine recrystallized from absolute ethanol and dried in a vacuum oven at 80° C. melted at 164°–165° C.

A mixture containing 8.5 g. of [6-methyl-5-(4-pyridinyl)pyridin-2-yl]hydrazine, 3 g. of Raney nickel and 200 ml. of methanol was placed in a Parr hydrogenation apparatus and treated at 60° C. under catalytic hydrogenation conditions for eight hours and then allowed to cool. The reaction mixture was filtered and the filtrate concentrated in vacuo to remove the solvent. The solid residue was slurried with acetonitrile, collected, recrystallized from propionitrile using decolorizing charcoal and dried to produce 4.7 g. of 6-methyl-5-(4-pyridinyl)-pyridin-2-amine, m.p. 207°–209° C.

Acid-addition salts of 6-methyl-5-(4-pyridinyl)pyridin-2-amine are conveniently prepared by adding to a mixture of 2 g. of 6-methyl-5-(4-pyridinyl)pyridin-2-amine in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 6-methyl-5-(4-pyridinyl)pyridin-2-amine and the appropriate acid, e.g., lactic acid or hydrochloric acid, to prepare respectively the monolactate or monohydrochloride salt in aqueous solution.

Following the procedure described in Example B-1 but using in place of 2-chloro-5-(4-pyridinyl)pyridine a molar equivalent quantity of the appropriate 2-chloro-5-PY-pyridine, it is contemplated that the corresponding 5-PY-pyridin-2-amines of Examples B-3 and B-4 can be obtained.

B-3. 5-(2-Methyl-4-pyridinyl)pyridin-2-amine.
    B-4. 5-(3-Ethyl-4-pyridinyl)pyridin-2-amine.

Following the procedure described in Example B-2 but using in place of 2-chloro-6-methyl-5-(4-pyridinyl)pyridine a molar equivalent quantity of the appropriate 2-chloro-6-Q-5-PY-pyridine, it is contemplated that the corresponding 6-Q-5-PY-pyridin-2-amines of Examples B-5 through B-13 can be obtained.

B-5. 6-Ethyl-5-(4-pyridinyl)pyridin-2-amine.
    B-6. 6-Methyl-5-(4-pyridinyl)pyridin-2-amine.
    B-7. 6-n-Propyl-5-(4-pyridinyl)pyridin-2-amine.
    B-8. 6-Isopropyl-5-(4-pyridinyl)pyridin-2-amine.
    B-9. 6-n-Butyl-5-(4-pyridinyl)pyridin-2-amine.
    B-10. 6-Isobutyl-5-(4-pyridinyl)pyridin-2-amine.
    B-11. 5-(4-Pyridinyl)-6-tert.-butylpyridin-2-amine.
    B-12. 6-n-Pentyl-5-(4-pyridinyl)pyridin-2-amine.
    B-13. 6-Ethyl-5-(2-methyl-4-pyridinyl)pyridin-2-amine.

The usefulness of the compounds of formula I, or pharmaceutically acceptable acid-addition salts thereof, as cardiotonic agents is demonstrated by their effectiveness in standard pharmacological test procedures, for example, in causing a significant increase in the contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the isolated cat or guinea pig atria and papillary muscle procedure, the compounds of formula I or pharmaceutically acceptable acid-addition salts thereof at doses of 10, 30, 100 μg./ml., were found to cause significant increases, that is, greater than 25% (cat) or 30% (guinea pig) in papillary muscle force and significant increases, that is, greater than 25%(cat) or 30% (guinea pig), in right atrial force, while causing a lower percentage increase in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested at said dose levels by this procedure in the cat, the compound of Example B-1, namely 5-(4-pyridinyl)pyridin-2-amine, was found to cause respective increases in papillary muscle force and right atrial force of 51% and 44% at 10 μg/ml., 117% and 77% at 30 μg/ml. and 157% and 134% at 100 μg/ml. When tested by this procedure in the guinea pig, the compound of Example B-2, namely, 6-methyl-5-(4-pyridinyl)pyridin-2-amine, was found to cause respective increases in papillary muscle force and right atrial force of 132% and 78% at 10 μg/ml, 230% and 283% at 30 μg/ml and 298% and 479% at 100 μg/ml.

Disclosed and claimed in copending parent application Ser. No. 135,100, now U.S. Pat. No. 4,297,360, is a cardiotonic composition for increasing cardiac contractility, said composition comprising a pharmaceutically acceptable carrier and, as the active component thereof, the cardiotonic compound of formula I hereinabove or inter alia, the corresponding prior art 5-(3-pyridinyl)-pyridin-2-amine or pharmaceutically acceptable acid-addition salt thereof. Also disclosed and claimed in copending application Ser. No. 135,100, now U.S. Pat. No. 4,297,360, is the method for increasing cardiac contracility in a patient requiring such treatment which comprises administering to such patient a cardiotonically effective amount of the compound of formula I hereinabove or inter alia, the corresponding prior art 5-(3-pyridinyl)pyridin-2-amine or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. The compounds for oral administration also include capsules of absorbable material, such as gelatin, containing said active component with or without the addition of diluents or excipients.

Preparations for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:
1. A 5-PY-6-Q-pyridin-2-amine having the formula

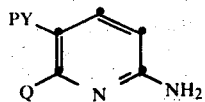

or pharmaceutically acceptable acid-addition salt thereof, where Q is hydrogen or lower-alkyl, and PY is 4-pyridinyl or 4-pyridinyl having one or two lower-alkyl substituents.

2. A compound according to claim 1 where Q is hydrogen, methyl or ethyl.

3. A compound according to claim 1 where PY is 4-pyridinyl.

4. 5-(4-Pyridinyl)pyridin-2-amine or pharmaceutically acceptable acid-addition salt thereof.

5. 6-Methyl-5-(4-pyridinyl)pyridin-2-amine or pharmaceutically acceptable acid-addition salt thereof.

* * * * *

UNITED STATES PATENT AND TRADEMARK OFFICE
CERTIFICATE OF CORRECTION

PATENT NO. : 4,420,617
DATED : December 13, 1983
INVENTOR(S) : G. Y. Lesher et al.

It is certified that error appears in the above-identified patent and that said Letters Patent is hereby corrected as shown below:

Column 2, line 52, "as in" should read -- as an --.

Column 3, line 2, "2(2H)-" should read -- 2(1H)- --.

Signed and Sealed this

Twenty-seventh Day of November 1984

[SEAL]

Attest:

GERALD J. MOSSINGHOFF

Attesting Officer     Commissioner of Patents and Trademarks